US00PP32638P2

(12) United States Plant Patent
Kerley et al.

(10) Patent No.: US PP32,638 P2
(45) Date of Patent: Dec. 15, 2020

(54) ***BEGONIA* PLANT NAMED 'KERBESPICUP'**

(50) Latin Name: ***Begonia* x *tuberhybrida***
Varietal Denomination: Kerbespicup

(71) Applicants: David William Kerley, Over (GB); Priscilla Grace Kerley, Over (GB); Timothy Edward Kerley, Willingham (GB); Sarah Elisabeth Kerley, Willingham (GB)

(72) Inventors: David William Kerley, Over (GB); Priscilla Grace Kerley, Over (GB); Timothy Edward Kerley, Willingham (GB); Sarah Elisabeth Kerley, Willingham (GB)

( * ) Notice: Subject to any disclaimer, the term of this patent is extended or adjusted under 35 U.S.C. 154(b) by 0 days.

(21) Appl. No.: 16/873,195

(22) Filed: Feb. 25, 2020

(51) Int. Cl.
*A01H 6/18* (2018.01)
*A01H 5/02* (2018.01)

(52) U.S. Cl.
USPC ..... Plt./346

(58) Field of Classification Search
USPC ..... Plt./346
CPC ..... A01H 6/18; A01H 5/02
See application file for complete search history.

*Primary Examiner* — Annette H Para
(74) *Attorney, Agent, or Firm* — C. A. Whealy

(57) ABSTRACT

A new and distinct cultivar of *Begonia* plant named 'Kerbespicup', characterized by its broadly upright to semi-trailing plant habit; roughly globular in plant form; moderately vigorous growth habit; freely basal branching habit; dark green-colored leaves; freely flowering habit; fragrant flowers; and large mostly double-type and occasional single-type flowers that are bright yellow in color.

2 Drawing Sheets

Figure 1:
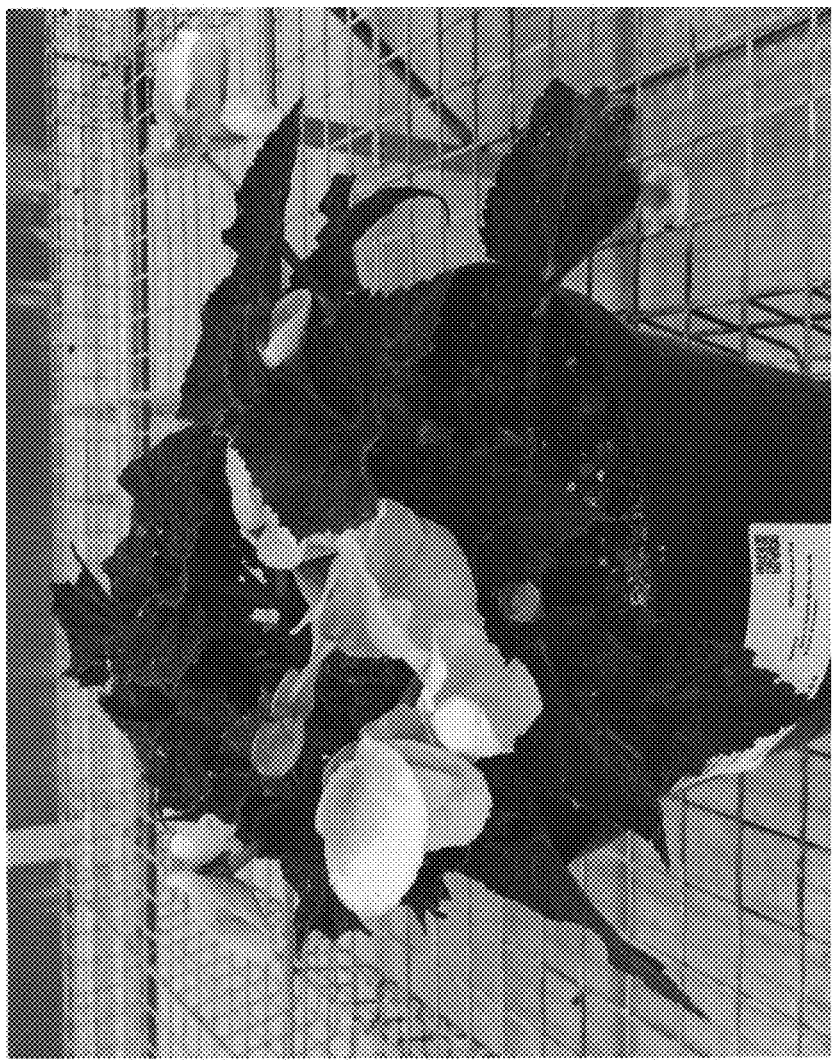

Botanical designation: *Begonia* x *tuberhybrida*.
Cultivar denomination: 'KERBESPICUP'.

BACKGROUND OF THE INVENTION

The present invention relates to a new and distinct cultivar of *Begonia* plant, botanically known as *Begonia* x *tuberhybrida* and hereinafter referred to by the name 'Kerbespicup'.

The new *Begonia* plant is a product of a planned breeding program conducted by the Inventors in Cambridge, United Kingdom. The objective of the breeding program is to create new *Begonia* plants with uniform plant habit and numerous attractive flowers.

The new *Begonia* plant is a naturally-occurring branch mutation of *Begonia* x *tuberhybrida* 'Kerbespicit', disclosed in U.S. Plant Pat. No. 29,308. The new *Begonia* plant was discovered and selected by the Inventors on a single flowering plant from within a population of plants of 'Kerbespicit' in a controlled greenhouse environment in Cambridge, United Kingdom in June, 2016.

Asexual reproduction of the new *Begonia* plant by terminal vegetative cuttings taken in a controlled greenhouse environment in Cambridge, United Kingdom since June, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Kerbespicup'. These characteristics in combination distinguish 'Kerbespicup' as a new and distinct *Begonia* plant:

1. Broadly upright to semi-trailing plant habit; roughly globular in plant form.
2. Moderately vigorous growth habit.
3. Freely basal branching habit.
4. Dark green-colored leaves.
5. Freely flowering habit.
6. Fragrant flowers.
7. Large mostly double-type and occasional single-type flowers that are bright yellow in color.

Plants of the new *Begonia* differ primarily from plants of the mutation parent, 'Kerbespicit', in flower color as plants of the new *Begonia* have darker yellow-colored flowers than plants of 'Kerbespicit'.

Plants of the new *Begonia* can be compared to plants of *Begonia* x *tuberhybrida* 'Fragrant Falls Lemon Fizz', not patented. In side-by-side comparisons conducted in Cambridge, United Kingdom, plants of the new *Begonia* differed primarily from plants of 'Fragrant Falls Lemon Fizz' in the following characteristics:

1. Plants of the new *Begonia* are more upright than plants of 'Fragrant Falls Lemon Fizz'.
2. Plants of the new *Begonia* have thinner stems than plants of 'Fragrant Falls Lemon Fizz'.
3. Plants of the new *Begonia* are more freely branching than plants of 'Fragrant Falls Lemon Fizz'.
4. Plants of the new *Begonia* are more freely flowering than plants of 'Fragrant Falls Lemon Fizz'.
5. Plants of the new *Begonia* have smaller flowers than plants of 'Fragrant Falls Lemon Fizz'.

Plants of the new *Begonia* can also be compared to plants of *Begonia* x *tuberhybrida* 'Scentiment Sunrise', not patented. In side-by-side comparisons conducted in Cambridge, United Kingdom, plants of the new *Begonia* differed primarily from plants of 'Scentiment Sunrise' in the following characteristics:

1. Plants of the new *Begonia* are more trailing than and not as upright as plants of 'Scentiment Sunrise'.
2. Plants of the new *Begonia* are more freely flowering than plants of 'Scentiment Sunrise'.
3. Flowers of plants of the new *Begonia* are not as pendulous as flowers of plants of 'Scentiment Sunrise'.
4. Plants of the new *Begonia* have smaller flowers than plants of 'Scentiment Sunrise'.
5. Plants of the new *Begonia* have bright yellow-colored flowers whereas plants of 'Scentiment Sunrise' have light orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'Kerbespicup' grown in a container.

Figure 2:
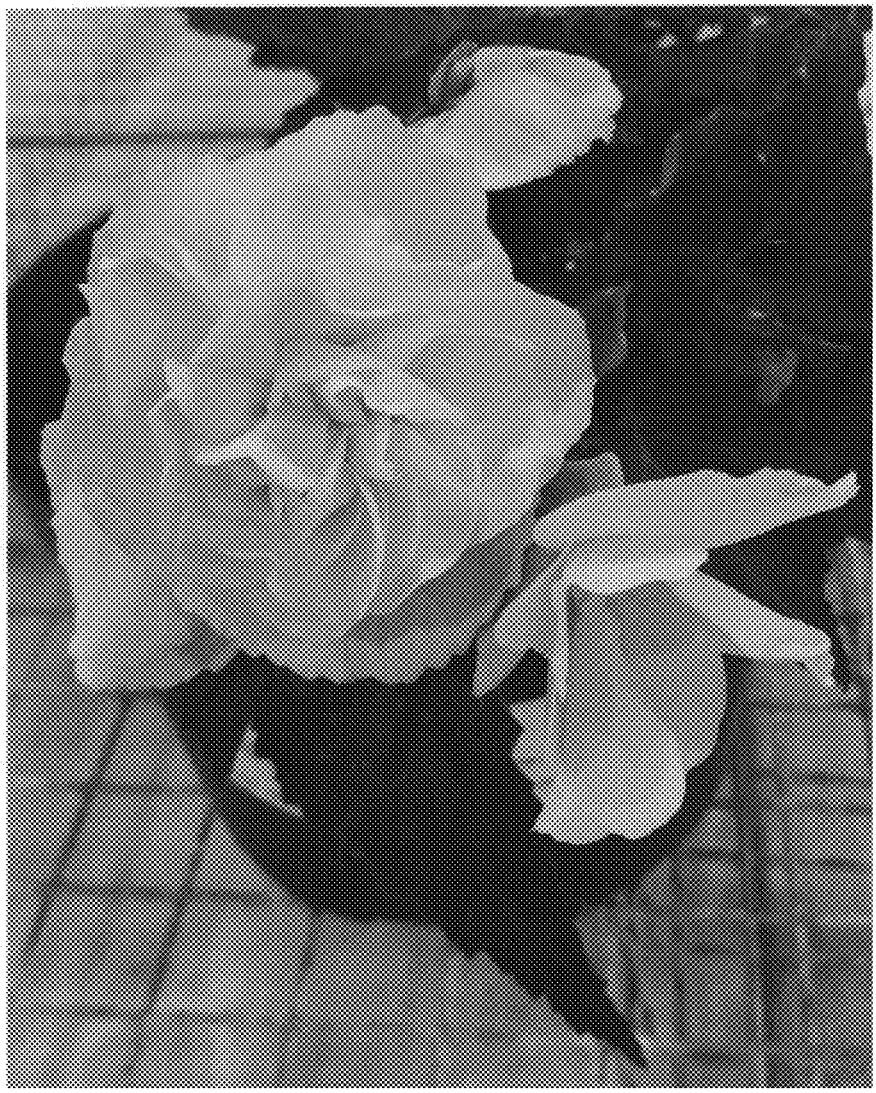

The photograph on the second sheet (FIG. 2 of 2) is a close up view of typical leaves and male double-type and female single-type flowers of 'Kerbespicup'.

DETAILED BOTANICAL DESCRIPTION

The aforementioned photographs and following observations and measurements describe plants grown during the autumn and winter in Loudon, N.H. with three plants in 21.6-cm containers in a glass-covered greenhouse in Loudon, N.H. and under cultural practices typical of commercial *Begonia* production. During the production of the plants, average daily temperatures ranged from 18° C. to 20° C. Plants were pinched six weeks after planting and were 15 weeks from planting when the photographs and description were taken. In the following description, color references are made to The Royal Horticultural Society Colour Chart, 2015 Edition, except were general terms of ordinary dictionary significance are used. Measurements were taken on individual plants.

Botanical classification: *Begonia* x *tuberhybrida* 'Kerbespicup'.

Parentage: Naturally-occurring branch mutation of *Begonia* x *tuberhybrida* 'Kerbespicit', disclosed in U.S. Plant Pat. No. 29,308.

Propagation:

*Type*.—By terminal vegetative cuttings.

*Time to initiate roots, summer*.—About 10 days at temperatures about 21° C.

*Time to initiate roots, winter*.—About 15 days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers to date.

Plant description:

*Plant habit and form*.—Broadly upright to semi-trailing plant habit; roughly globular in plant form.

*Growth habit*.—Moderately vigorous growth habit and moderate growth rate; suitable for 9-cm and larger containers.

*Branching habit*.—Freely basal branching habit, typically about three to five basal branches develop per plant; dense and bushy plant habit.

*Plant height*.—About 10 cm.

*Plant width*.—About 17 cm.

*Basal branches*.—Length: About 9 cm. Diameter: About 9 mm. Internode length: About 1.7 cm to 1.9 cm. Aspect: Mostly erect. Strength: Strong, flexible, bending with the weight of the flowers. Texture and luster: Moderately pubescent; slightly glossy. Color, developing: Close to 148A; at the internodes, close to 183A. Color, developed: Close to 184A variably overlain with close to 183A.

*Leaves*.—Arrangement: Alternate; simple. Length: About 15.5 cm. Width: About 7 cm. Shape: Obliquely cordate. Apex: Long acuminate. Base: Oblique cordate, lobes typically free to occasionally imbricate. Margin: Serrate; not undulate. Texture and luster, upper surface: Sparsely pubescent; slightly velvety; semi-glossy. Texture and luster, lower surface: Mostly glabrous with pubescent along venation; slightly velvety; semi-glossy. Venation pattern: Palmate. Color: Developing leaves, upper surface: Close to 147A variably overlain with close to 187A to 187B. Developing leaves, lower surface: Close to 146A variably overlain with close to 183A to 183B. Fully expanded leaves, upper surface: Close to between 147A and N189A; venation, close to 144A and 146A. Fully expanded leaves, lower surface: Close to 146A variably overlain with close to 183A to 183B; venation, close to 144A and 146A. Petioles: Length: About 2.5 cm to 2.75 cm. Diameter: About 4 mm by 5 mm. Texture and luster, upper and lower surfaces: Moderately pubescent; slightly glossy. Strength: Strong, flexible. Color, upper and lower surfaces: Close to 148A variably overlain with close to 183A. Stipules: Quantity and appearance: Two leafy stipules positioned at base of the leaf petiole. Length: About 1.2 cm. Width: About 7 mm. Shape: Deltoid. Apex: Acute. Base: Truncate. Margins: Finely ciliate. Texture and luster, upper and lower surfaces: Smooth, glabrous; moderately glossy. Color, upper and lower surfaces: Close to 144A.

Flower description:

*Flower form and flowering habit*.—Large rotate flowers arranged in axillary clusters with typically two or three flowers per cluster; flowers face outwardly to slightly nodding and are positioned at, above and beyond the foliar plane; flowers mostly double-types and occasionally single-types develop.

*Natural flowering season*.—Plants flower continuously from the spring into the autumn in New Hampshire.

*Flower longevity*.—Individual flowers last about ten days on the plant; flowers not persistent.

*Fragrance*.—Fragrant, lemon-like.

*Flower buds*.—Length: About 1.5 cm. Diameter: About 2 cm. Shape: Lenticular, flattened. Texture and luster: Smooth, glabrous; velvety; semi-glossy. Color: Close to between 144A and 146A.

*Male flowers*.—Diameter: About 3 cm. Depth: About 3.5 cm. Shape: Double, almost spherical. Tepals and tepaloids: Quantity and arrangement: About 60 to 80 arranged in numerous whorls. Length, outer whorl: About 2.5 cm to 2.8 cm. Width, outer whorl: About 2.3 cm to 2.5 cm. Shape: Spatulate. Apex: Obtuse. Base: Cuneate. Margin: Entire, not undulate. Texture and luster, upper and lower surfaces: Smooth, glabrous; somewhat velvety; slightly glossy. Color: When opening, upper and lower surfaces: Close to 8D; towards the base, close to 144A. Fully opened, upper surface: Close to 9A, towards the base, close to 144A; venation, similar to lamina; color does not change with development. Fully opened, lower surface: Close to 8C; venation, similar to lamina; color does not change with development.

*Female flowers*.—Diameter: About 4 cm to 4.5 cm. Depth: About 1.8 cm to 2.2 cm. Shape: Single, rotate. Tepals: Quantity and arrangement: Five in a single whorl; no tepaloids develop on female flowers. Length: About 2.5 cm to 2.8 cm. Width: About 2.3 cm to 2.5 cm. Shape: Spatulate. Apex: Obtuse. Base: Cuneate. Margin: Entire, not undulate. Texture and luster, upper and lower surfaces: Smooth, glabrous; somewhat velvety; slightly glossy. Color: When opening, upper and lower surfaces: Close to 8D; towards the base, close to 144A. Fully opened, upper surface: Close to 9A, towards the base, close to 144A; venation, similar to lamina; color does not change with development. Fully opened, lower surface: Close to 8C; venation, similar to lamina; color does not change with development.

*Flower bracts*.—Quantity and arrangement: Two positioned at the top of the peduncle. Length: About 1.8 cm. Width: About 2.7 cm. Shape: Roughly reniform. Apex: Obtuse. Base: Cordate. Margin: Entire. Texture and luster, upper and lower surfaces: Smooth, glabrous; moderately glossy. Color, upper surface: Close to 144A. Color, lower surface: Close to between 144A and 146A.

*Peduncles*.—Length: About 2.4 cm to 2.8 cm. Diameter: About 3 mm. Angle: Outward to slightly drooping. Strength: Flexible, bending with the weight of the flowers. Texture and luster: Smooth, glabrous; moderately glossy. Color: Close to N144A.

*Reproductive organs*.—Stamens: Stamen development has not been observed on male or double-type flowers and not observed on female or single-type flowers. Pistils (present on female flowers only): Quantity per flower: About six, fused in pairs. Pistil length: About 4 mm. Style length: About 3.5 mm. Style color: Close to 12A. Stigma diameter: About 2.5 mm by 2 mm, irregular in shape. Stigma color: Close to 12A. Ovary color: Close to 144A.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

It is claimed:

1. A new and distinct *Begonia* plant named 'Kerbespicup' as illustrated and described.

* * * * *